United States Patent [19]

Domb

[11] Patent Number: 5,660,851
[45] Date of Patent: Aug. 26, 1997

[54] OCULAR INSERTS

[75] Inventor: Abraham Jacob Domb, Efrat, Israel

[73] Assignee: Yissum Research Development Company of the Hebrew Univ. of Jerusalem, Jerusalem, Israel

[21] Appl. No.: 464,330

[22] Filed: Jun. 5, 1995

Related U.S. Application Data

[63] Continuation-in-part of Ser. No. 20,168, Feb. 22, 1993, Pat. No. 5,498,729, which is a continuation of Ser. No. 456,376, Dec. 26, 1989, abandoned.

[51] Int. Cl.$^6$ .................................................. A61F 2/00
[52] U.S. Cl. ........................ 424/427; 424/428; 528/271
[58] Field of Search ................................ 424/427, 428; 528/271

[56] References Cited

U.S. PATENT DOCUMENTS

| | | | |
|---|---|---|---|
| 3,618,604 | 11/1971 | Ness | 128/260 |
| 3,625,214 | 12/1971 | Higuchi | 128/260 |
| 3,626,940 | 12/1971 | Zaffarone | 128/260 |
| 3,630,200 | 12/1971 | Higuchi | 128/260 |
| 3,811,444 | 5/1974 | Heller et al. | 128/260 |
| 3,914,402 | 10/1975 | Shell | 424/32 |
| 3,960,150 | 6/1976 | Hussain et al. | 128/260 |
| 3,981,303 | 9/1976 | Higuchi et al. | 128/260 |
| 3,986,510 | 10/1976 | Higuschi et al. | 424/428 |
| 3,991,759 | 11/1976 | Urquhart | 128/260 |
| 3,993,071 | 11/1976 | Higuchi et al. | 128/260 |
| 3,995,635 | 12/1976 | Higuchi et al. | 128/260 |
| 4,014,987 | 3/1977 | Heller et al. | 424/15 |
| 4,093,709 | 6/1978 | Choi et al. | 424/19 |
| 4,180,064 | 12/1979 | Heller et al. | 128/130 |
| 4,180,646 | 12/1979 | Choi et al. | 528/153 |
| 4,190,642 | 2/1980 | Gale et al. | 424/19 |
| 4,248,855 | 2/1981 | Blank et al. | 424/19 |
| 4,249,531 | 2/1981 | Heller et al. | 128/260 |
| 4,271,143 | 6/1981 | Schoenwald et al. | 424/78 |
| 4,281,654 | 8/1981 | Shell et al. | 128/260 |
| 4,303,637 | 12/1981 | Shell et al. | 424/14 |
| 4,304,765 | 12/1981 | Shell et al. | 424/14 |
| 4,327,725 | 5/1982 | Cortese et al. | 128/260 |
| 4,346,709 | 8/1982 | Schmitt | 128/260 |
| 4,407,792 | 10/1983 | Schoenwald et al. | 424/81 |
| 4,415,551 | 11/1983 | Fang | 424/65 |
| 4,432,964 | 2/1984 | Shell et al. | 424/14 |
| 4,449,983 | 5/1984 | Cortese et al. | 604/892 |
| 4,472,427 | 9/1984 | Baldwin et al. | 424/282 |
| 4,478,818 | 10/1984 | Shell et al. | 424/14 |
| 4,519,801 | 5/1985 | Edgren | 604/892 |
| 4,522,829 | 6/1985 | Harting et al. | 514/652 |
| 4,553,973 | 11/1985 | Edgren | 604/892 |
| 4,730,013 | 3/1988 | Bondi et al. | 524/42 |
| 4,765,977 | 8/1988 | Baron | 424/78 |
| 4,789,724 | 12/1988 | Domb et al. | 528/176 |
| 4,857,311 | 8/1989 | Domb et al. | 424/78 |
| 4,863,457 | 9/1989 | Lee | 604/891.1 |
| 4,888,176 | 12/1989 | Langer et al. | 424/426 |
| 4,911,920 | 3/1990 | Jani et al. | 424/78 |
| 4,940,588 | 7/1990 | Sparks et al. | 424/490 |
| 4,952,402 | 8/1990 | Sparks et al. | 424/419 |
| 4,966,773 | 10/1990 | Gressel et al. | 424/489 |
| 5,075,104 | 12/1991 | Gressel et al. | 424/78.04 |
| 5,137,728 | 8/1992 | Bawa | 424/427 |
| 5,147,647 | 9/1992 | Darougar | 424/427 |
| 5,171,812 | 12/1992 | Domb | 526/318.2 |
| 5,173,298 | 12/1992 | Meadows | 424/427 |
| 5,175,235 | 12/1992 | Domb et al. | 525/329.7 |
| 5,182,102 | 1/1993 | DeSantis, Jr. et al. | 424/78.1 |
| 5,192,535 | 3/1993 | Davis et al. | 424/78.04 |
| 5,206,341 | 4/1993 | Ibay et al. | 528/361 |
| 5,209,927 | 5/1993 | Gressel et al. | 424/78.04 |
| 5,212,162 | 5/1993 | Missel et al. | 514/54 |
| 5,225,196 | 7/1993 | Robinson | 424/427 |
| 5,240,963 | 8/1993 | Domb et al. | 514/772.6 |
| 5,270,419 | 12/1993 | Domb | 526/318.2 |
| 5,340,572 | 8/1994 | Patel et al. | 424/78.04 |
| 5,354,556 | 10/1994 | Sparks et al. | 424/419 |
| 5,384,333 | 1/1995 | Davis et al. | 514/772.3 |

FOREIGN PATENT DOCUMENTS

WO91/16869  11/1991  WIPO.

OTHER PUBLICATIONS

Atherton, E., et al., "Peptide Synthesis. Part 12. 3,4–Dihydro–4–oxo–1,2,3–Benzotriazin–3–yl Esters of Fluorenylmethoxycarbonyl Amino Acids as Self–Indicating Reagents for Solid Phase Peptide Synthesis," *J. Chem. Soc., Perkin Trans.*, 1:2887–2894 (1988).

Brewer, J.H., et al., "Sterilization," *Remington's Pharmaceutical Sciences*, vol. XIV, pp. 1501–1518 (1970).

Ertain, M., et al., "Synthesis and Antipseudomonal Activities of Some Ofloxacin Esters as Prodrugs," *Arzneimittel–Forschung/Drug Research*, 42(I), Nr. 1, pp. 70–72 (1992).

Guerin, P., et al., "Drug Carriers," *Polymer Bulletin*, 14:187–192 (1985).

Guerin, Ph., et al., "Benzyl Esters of Optically Active Malic Acid Stereocopolymers as Obtained by Ring–Opening Polymerization of (R)–(+) and (S)–(–)–Benzyl Malolatonates," *Makromol. Chem. Macromol. Symp.*, 6:305–314 (1986).

(List continued on next page.)

*Primary Examiner*—Mark D. Sweet
*Attorney, Agent, or Firm*—Kilpatrick Stockton LLP

[57] ABSTRACT

Absorbable ocular inserts fabricated of materials that are biologically inert, biodegradable, non-allergenic, and insoluble in tear liquid, and a method for delivering substances to the eye using the ocular insert, are disclosed. In embodiment A of the invention, the insert and method include the covalent attachment of a carboxylic acid-containing substance to be delivered to a polymer that contains pendent carboxylic acid groups, through anhydride linkages. The drug is released over time by hydrolysis of the anhydride bonds. In embodiment B of the invention, a substance to be delivered (whether or not it contains a carboxylic acid group) is dispersed within an anhydride polymer or copolymer matrix and the mixture is formed into an appropriately shaped article for ocular delivery. In embodiment C of the invention, the insert and method include the covalent attachment of a carboxylic acid-containing substance to be delivered to a polymer that contains pendent carboxylic acid groups through methylene diester bonds which degrade in vivo over time.

18 Claims, 3 Drawing Sheets

OTHER PUBLICATIONS

Jampel, Henry D., et al., "Glaucoma Filtration Surgery in Nonhuman primates Using Taxol and Etoposide in Polyanhydride Carriers," *Investigative Ophthalmology & Visual Science*, 34(11):3076–3083 (1993).

Knorr, R., et al., "New Coupling Reagents in Peptide Chemistry", *Tetrahedron Lett.*, 30(15):1927–1930 (1989).

Larock, "Comprehensive Organic Transformation," VCH Publishers, New York (1989) (Table of Contents only).

Maeda, Y., et al., "Effects of Aluminium–Containing Antacid on Bioavailability of Ofloxacin Following Oral Administration of Pivaloyloxymethyl Ester of Ofloxacin as Prodrug," *Biol. Pharm. Bull.*, 16(6):594–599 (1993).

*The Merck Index*, 14th edition, Merck & Co., Inc., New Jersey (1989), examples of carboxylic acid–containing bioactive compounds.

Patai, S., ed. *The Chemistry of Acid Derivatives*, part 1, Wiley, New York (1979) (book).

Reid, G.E. and Simpson, R.J., "Automated Solid–Phase Peptide Synthesis: Use of 2–(1H–Benzotriazol–1–yl)–1,1,3,3,–tetramethyluronium Tetrafluoroborate for Coupling of tert–Butyloxycarbonyl Amino Acids," *Ann. Biochem.*, 200:301–309 (1992).

Rivaille, P., et al., "Synthesis of LH–RH Using a New Phenolic Polymer as Solid Support and Bop Reagent for Fragment Coupling," *Tetrahedron Lett.*, 36:3413–3419 (1980).

Rasmussen, M. and Leonard, N.J., "The Synthesis of 3–(2'–Deoxy–D–Ribofuranosyl) Adenine. Application of a New Protecting Group, Pivaloyloxymethyl (Pom)[1]", *J. Amer. Chem. Soc.*, 89(21):5439–5445 (1967).

Roberts, J.D. and Caserio, M.C., editors in the *Basic Principles of Organic Chemistry*, California Institute of Technology, W.A. Benjamin, Inc., publishers, New York (1965) (Table of Contents only).

Schön, I. and Kisfaludy, L., "9 Fluorenylmethyl Pentafluorophenyl Carbonate as a Useful Reagent for the Preparation of N–9–Fluorenylmethyloxycarbonylamino Acids and Their Pentafluorophenyl Esters," *Synthesis*, pp. 303–305 (1986).

Tamargo, Rafael J., et al., "Growth Inhibition of the 9L Glioma Using Polymers to Release Heparin and Cortisone Acetate," *Journal of Neuro–Oncology*, 9:131–138 (1990).

□ Eudragit anhydride
○ Eudragit anhyd. + 10% Ibuprofen
□ Ibuprofen bound Eudragit
△ Eudragit L

OCULAR INSERTS

This application is a continuation-in-part of U.S. Ser. No. 08/020,168, filed on Feb. 22, 1993, by Abraham J. Domb, et al., now U.S. Pat. No. 5,498,729 which is a continuation of U.S. Ser. No. 07/456,376, filed on Dec. 26, 1989, by Abraham J. Domb, et al now abandoned. This invention is in the area of polymeric delivery devices.

BACKGROUND OF THE INVENTION

Ocular inserts are becoming a popular means to deliver a wide range of drugs to the eye. The inserts are typically in an initial shape and size to be inserted and retained in any appropriate region of the eye. The inserts release the drug over time in a controlled fashion.

Two ophthalmic inserts that have been developed for commercial use are the OCUSERT system (Alza Corporation) and Lacrisert (Merck Corporation). The OCUSERT device is designed to provide for the release of medication at predetermined and predictable rates, which permits the elimination of frequent dosing by the patient, ensures nighttime medication, and provides a better means of patient compliance. The insert is elliptical with dimensions of 13.4 by 4.7 mm and 0.3 mm in thickness. The insert is flexible and is a multilayered structure consisting of a drug-containing core surrounded on each side by a layer of copolymer membranes through which the drug diffuses at a constant rate. The rate of drug diffusion is controlled by the polymer composition, the membrane thickness, and the solubility of the drug. The devices are sterile and do not contain preservatives. OCUSERT inserts containing pilocarpine are widely used in glaucoma therapy. After placement in the conjunctival sac, the inserts are designed to release medication at the desired rates over a 7-day period at which time they are removed and replaced with new ones.

The Lacrisert insert is a sterile, translucent, rod-shaped, water-soluble form of hydroxypropyl cellulose. The product is inserted into the inferior cul-de-sac of the eye of patients with dry eye states. The insert acts to stabilize and thicken the precorneal tear film and to delay its breakup. Inserts are typically placed in the eye once or twice daily. Following administration, the inserts soften and slowly dissolve.

The following U.S. patents disclose ocular inserts for medicinal therapy. U.S. Pat. No. 4,730,013 to J.V. Bondi, et al., assigned to Merck & Company, Inc., discloses ocular inserts with or without pharmaceutically active agents, comprising 75% to 100% of a matrix of 15% polyvinyl alcohol, 10% glycerine, 75% hydroxy propyl methylcellulose phthalate, and 0–25% of a pharmacologically active agent.

U.S. Pat. No. 4,522,829 to Andreas Fuchs, et al., (Merck Patent gmbh de), discloses an intraocular pressure-lowering film insert of a 1-(p-2-iso-propoxyethoxy methyl-phenoxy) -3-isopropylamino-propan-2-ol or a physiologically acceptable salt thereof and an ophthalmically acceptable carrier.

U.S. Pat. No. 4,432,964 to Robert M. Gale (Alza Corp.) discloses an ocular insert for treating inflammation made of a pair of micronized steroids consisting of two topically acceptable different chemical therapeutic forms of betamethasone or a derivative, and a bio-erodible polymeric polyorthoester carrier.

U.S. Pat. No. 4,346,709 to Edward E. Schmitt (Alza Corp.) discloses an erodible device for delivering a drug to an environment of use, which includes a poly(orthoester) or a poly(orthocarbonate).

U.S. Pat. No. 4,303,637 to Robert M. Gale, et al., discloses an ocular insert composed of a beta blocking drug in a polymer with the drug surrounded by the polymer selected from the group consisting of poly(olefin), poly(vinylolefin), poly(haloolefin), poly(styrene), poly(vinyl), poly(acrylate), poly(methacrylate), poly(oxide), poly(ester), poly(amide), and poly(carbonate).

U.S. Pat. No. 4,190,642 (Alza Corp.) discloses an ocular insert composed of a discrete depot of a pilocarpine solute and an epinephrine solute, a film of an ethylene-vinyl ester copolymer forming the insert, where fluid from the environment is imbibed through the wall into the depots to continually dissolve the solutes and release the formulation.

U.S. Pat. No. 4,093,709 to Nam S. Choi (Alza Corp.) discloses an ocular insert composed of an orthoester and an orthocarbonate polymer.

U.S. Pat. No. 3,993,071, issued Nov. 23, 1976 to Takeru Higuchi, et al., discloses a bio-erodible ocular insert for the controlled administration of a drug to the eye from 8 hours to 30 days, in which the drug formulation can also be microencapsulated and the microcapsules dispersed in the drug release rate controlling material.

U.S. Pat. No. 3,981,303 to Takeru Higuchi, et al. (Alza Corp.) discloses an ocular insert for the continuous controlled administration of a drug to the eye composed of a plurality of microcapsule reservoirs comprised of a drug formulation confined within a drug release rate controlling material, distributed throughout a bio-erodible matrix permeable to the passage of the drug at a higher rate than the rate of drug passage through the drug release rate controlling material, where the device is of an initial shape and size that is adapted for insertion and retention in the sac of the eye. The hydrophobic material may be selected from cholesterol, waxes, $C_{10}$ to $C_{20}$ fatty acids, and polyesters, and the drug may be selected from epinephrine, pilocarpine, hydrocortisone, idoxuridine, tetracycline, polymixin, gentamycin, neomycin, and dexamethasone.

U.S. Pat. No. 3,960,150 to Takeru Higuchi, et al. (Alza Corp.) discloses an ocular insert for the continuous Controlled administration of a drug to the eye composed of a body of hydrophobic bio-erodible drug release rate controlling material containing a drug, where the body is of an initial shape adapted for insertion in the sac of the eye, where the drug release rate controlling material can be a polyester, and the drug may be selected from epinephrine, pilocarpine, hydrocortisone, idoxuridine, tetracycline, polymixin, gentamycin, neomycin, and dexamethasone, and derivatives.

U.S. Pat. No. 3,811,444, issued May 21, 1974 to Richard W. Baker, et al., assigned to the Alza Corp., discloses an ocular insert for the continuous controlled administration of a drug to the eye comprising a drug formulation dispersed through a body of selected hydrophobic polycarboxylic acid which erodes over time to dispense the desired amount of drug. The polycarboxylic acid can be a copolymer of an acid from the group of maleic acid, acrylic acid, lower alkyl acrylic acids from about 4 to about 6 carbon atoms, with a copolymerizable olefinically unsaturated material selected from the group consisting of ethylene, propylene, butadiene, isoprene and styrene and the lower alkyl vinyl ethers.

U.S. Pat. No. 3,630,200, issued Dec. 28, 1971, to Takeru Higuchi, assigned to the Alza Corporation, discloses a drug-dispensing ocular insert for insertion into the cul-de-sac of the conjunctiva between the sclera of the eyeball and the lid where the inner core contains the drug and is surrounded by a soft hydrophilic outer layer, where the outer layer can be composed of a polymer selected from the group consisting of hydrophilic hydrogel of an ester of acrylic or methacrylic acid, modified collagen, cross-linked hydrophilic polyether gel, cross-linked polyvinyl alcohol, and cross-linked partially hydrolyzed polyvinyl acetate and cellulosic gel. The inner core may be a polymer selected from the group of plasticized or unplasticized polyvinylchloride, plasticized nylon, unplasticized soft nylon, silicone rubber, polyethylene, hydrophilic hydrogel of an ester of acrylic or methacrylic acid, modified collagen, cross-linked hydrophilic polyether gel, cross-linked polyvinyl alcohol, crosslinked partially-hydrolyzed polyvinylacetate, cellulosic gel, ion-exchange resin and plasticized polyethylene terephthalate.

U.S. Pat. No. 3,618,604 to Richard A. Mess (Alza Corporation) discloses a drug-dispensing ocular insert adapted for insertion into the cul-de-sac of the eye, where the insert is a tablet containing a reservoir of drug formulation within a flexible polymeric material, and the polymeric material is formed of plasticized or unplasticized polyvinylchloride, plasticized nylon, unplasticized soft nylon, plasticized polyethylene terephthalate, silicon rubber, hydrophilic hydrogel of a ester of acrylic or methacrylic acid, modified collagen, cross-linked hydrophilic polyether gel, cross-linked polyvinyl alcohol, and cross-linked partially-hydrolyzed polyvinylacetate.

U.S. Pat. Nos. 3,993,071; 3,986,510; 3,981,303, 3,960,150, and 3,995,635 to Higuchi, et al., disclose a biodegradable ocular insert made from zinc alginate, poly(lactic acid), poly(vinyl alcohol), poly(anhydrides), and poly(glycolic acid).

A number of patents disclose the use of drug-loaded polyanhydrides (wherein the anhydride is in the backbone of the polymer) as matrix materials for ocular inserts. See, in general, U.S. Pat. Nos. 5,270,419; 5,240,963; and 5,137,728. Other U.S. Patents that describe the use of polyanhydrides for controlled delivery of substances include: U.S. Pat. No. 4,857,311 to Domb and Langer, entitled "Polyanhydrides with Improved Hydrolytic Degradation Properties," which describes polyanhydrides with a uniform distribution of aliphatic and aromatic residues in the chain, prepared by polymerizing a dicarboxylic acid with an aromatic end and an aliphatic end); U.S. Pat. No. 4,888,176 to Langer, Domb, Laurencin, and Mathiowitz, entitled "Controlled Drug Delivery High Molecular Weight Polyanhydrides," which describes the preparation of high molecular weight polyanhydrides in combination with bioactive compounds for use in controlled delivery devices); and U.S. Pat. No. 4,789,724 to Domb and Langer, entitled "Preparation of Anhydride Copolymers," which describes the preparation of very pure anhydride copolymers of aromatic and aliphatic diacids.

U.S. Pat. No. 5,075,104 discloses an ophthalmic carboxyvinyl polymer gel for the treatment of dry eye syndrome.

U.S. Pat. No. 4,407,792 discloses an aqueous gel that includes a gel-forming amount of an ethylene-maleic anhydride polymer.

U.S. Pat. No. 4,248,855 discloses the salt of pilocarpine with a polymer containing acid groups for use as an ocular insert, among other things.

U.S. Pat. Nos. 4,180,064 and 4,014,987 disclose the use of poly(carboxylic acids) or their partially esterified derivatives as drug delivery devices.

PCT/US90/07652 (which claims priority to U.S. Ser. No. 07/456,376, to which this application also claims priority) discloses that biologically active compounds containing a carboxylic acid group can be delivered in the form of an anhydride of a carrier molecule that modifies the properties of the molecule.

Although these patents disclose a number of types of ocular inserts, there is still a need to provide new inserts with modified properties for the delivery of substances. In particular, there is a need to provide inserts that act as long acting absorbable inserts for the delivery of anti-inflammatory and antibiotic drugs to the eye, wherein the polymer carrier is eliminated simultaneously with the drug. The preferred polymeric matrix combines the characteristics of hydrophobicity, stability, strength, flexibility, low melting point, and suitable degradation profile. The polymer must be hydrophobic so that it retains its integrity for a suitable time when placed in an aqueous environment, such as the eye, and stable enough to be stored for an extended period before use. The polymer must be strong, yet flexible enough that it does not crumble or fragment during use.

It is therefore an object of the present invention to provide ocular inserts that act as long acting absorbable inserts for the delivery of substances to the eye, wherein the polymer carrier is eliminated simultaneously with the drug.

It is another object of the present invention to provide ocular inserts that act as long acting absorbable inserts for the delivery of anti-inflammatory and antibiotic drugs to the eye, wherein the polymer carrier is eliminated simultaneously with the drug.

It is still another object of the present invention to provide a method for the controlled delivery of substances to the eye.

It is yet a further object of the present invention to provide an absorbable polymeric insert for the controlled release of biologically active compounds for periods from 1 to 7 days after a single administration, without the need to remove the device after the compound has been released.

SUMMARY OF THE INVENTION

Absorbable ocular inserts fabricated of materials that are biologically inert, biodegradable, non-allergenic, and insoluble in tear liquid, and a method for delivering substances to the eye using the ocular insert, are disclosed. In embodiment A of the invention, the insert and method include the covalent attachment of a carboxylic acid-containing substance to be delivered to a polymer that contains pendent carboxylic acid groups, through anhydride linkages. The drug is released over time by hydrolysis of the anhydride bonds. The polymer-substance anhydride is initially hydrophobic. As the substance is hydrolysed from the polymeric backbone, the polymer is converted to a polycarboxylic acid that is hydrophilic and which is removed from the eye through the tearing process.

Any pharmaceutically acceptable polymer that has carboxylic acid substituent groups can be used to prepare the anhydride. Suitable polycarboxylic acids include, but are not limited to, acrylic acid based polymers, such as polymers and copolymers of (meth)acrylic acid, and polymers and copolymers of maleic acid or vinylacetic acid. Preferred polyacids are poly(methacrylic acid-methylmethacrylate) copolymers (Eudragit) and poly(acrylic acids) (PAA), which are commercially available in various molecular weights. Polycarboxylic acids can also be prepared by esterification or partial esterification or anhydride formation of polyacrylic acids with compounds containing more than one carboxylic acid (such as citric acid) to vary the properties of the polymer or simply increase the number of carboxylic acid groups in the polymer.

In embodiment B of the invention, a substance to be delivered (whether or not it contains a carboxylic acid group) is dispersed within an anhydride polymer or copolymer matrix and the mixture is formed into an appropriately shaped article for ocular delivery. The polyanhydride can be prepared from any polyacid, including polymers and copolymers of (meth)acrylic acid, and polymers and copolymers of maleic acid or vinylacetic acid. The copolymer can include any other desired monomer, including but not limited to (meth)acrylate, maleate, or vinyl acetate. The substance is released over time, and the polyanhydride is simultaneously hydrolysed to a polyacid, which is removed from the eye in the tearing process. The substances to be incorporated should not chemically interact with the polymer during fabrication, or during the release process.

In embodiment C of the invention, the insert and method include the covalent attachment of a carboxylic acid-containing substance to be delivered to a polymer that contains pendent carboxylic acid groups through methylene diester bonds which degrades in vivo over time.

The ocular insert is sized, shaped and adapted for easy insertion and prolonged retention in the eye for administration of a therapeutically effective amount of the substance to be delivered. The insert can be any desired shape, including but not limited to a thin flexible film, a microparticle (for example, a microsphere, nanosphere, or microcapsule), a rod, and a disc. The insert can be prepared in any desired thickness and width. In one embodiment, the thickness of the insert is between approximately 0.01 and 2 mm and the width of the device is between 5 and 100 mm$^2$.

In an alternative embodiment, fatty acid residues can be attached through anhydride linkages to any of the polymers used in the various embodiments to increase the hydrophobicity of the polymer. Any number of fatty acid residues can be added that achieves the desired result. As a nonlimiting example, polymethacrylic acid can be converted to a mixed anhydride in which a number of the pendant carboxylic acids are converted to fatty acid anhydrides and a number of carboxylic acid groups are converted to anhydrides of carboxylic-acid containing drugs.

Additionally, the polymers can be crosslinked as desired, directly or through any appropriate linker moiety.

The period of time of release, and kinetics of release, of the substance from the insert will vary depending on the polymer properties, size of the device, the substrate, additives, and the method of incorporation of the substrate in the polymer. Those of ordinary skill in this art will be able to select the appropriate polymer or combination of polymers or optionally, additives, to achieve a desired effect. In one embodiment, additives such as inorganic salts, BSA (bovine serum albumin), polyethylene glycol, and inert organic compounds are used to alter the profile of substance release.

In embodiments A and C, the drug release rate and clearance rate of the device from the eye is influenced by the amount of drug covalently bound to the polymer (drug loading), the molecular weight of the drug and of the polymer, the hydrophilicity of the polymer carrier, the additives in the film, if any, and the polymer architecture, method of preparation, size and geometry of the device.

In embodiment A, the drug release rate is primarily determined by the hydrolysis rate of the anhydride bond between the drug and the polymer, rather than by the size of the device. In embodiment C, the drug release rate is primarily determined by the hydrolysis rate of the methylene diester bonds between the drug and the polymer.

Release of substrate in embodiment B is achieved by diffusion or erosion (including degradation) of the polymer matrix, or by a combination of diffusion and erosion. The permeability of polymer, and thus the diffusion rate, can be reduced by introduction or addition of hydrophobic units into the polymer, or by the addition of hydrophobic substances or polymers, such as kaolin, talc, magnesium trisilicate, and polylactide, into the material to be fabricated. The permeability can be increased by the addition of hydrophilic polymers, such as polyethylene glycol, sugar, and poly(vinyl pyrrolidone), or by modifying the polymer with hydrophilic substituents. A substance to be delivered can be incorporated into the matrix of the poly(meth)acrylate anhydride matrix by any appropriate method, including solution fabrication, melt fabrication, and compression molding.

In a preferred embodiment, the delivery device provides the controlled release of bioactive compounds for periods of between approximately one and seven days after a single administration, without the need to remove the device after the compound has been released.

Any biologically acceptable substance can be delivered using these methods and compositions. If the substance contains a carboxylic acid group, embodiments A, B or C can be used. If, alternatively, the substance does not contain a carboxylic acid group, embodiment B should be selected.

Polymers of any molecular weight can be used in the process that provides a delivery device with the desired properties. A preferred range is 1,000 to 10,000,000 Da. Eudragit NE 30 D has a molecular weight ranging from 40 to 800 KDa.

Delivery devices prepared according to this process can also be used to deliver water soluble or water insoluble drugs such as nonsteroidal anti-inflammatory compounds, anesthetics, chemotherapeutic agents, immunosuppressive agents, steroids, antibiotics, antivirals, antifungals, steroidal antiinflammatories, and anticoagulants.

DETAILED DESCRIPTION OF THE INVENTION

Figure 1:
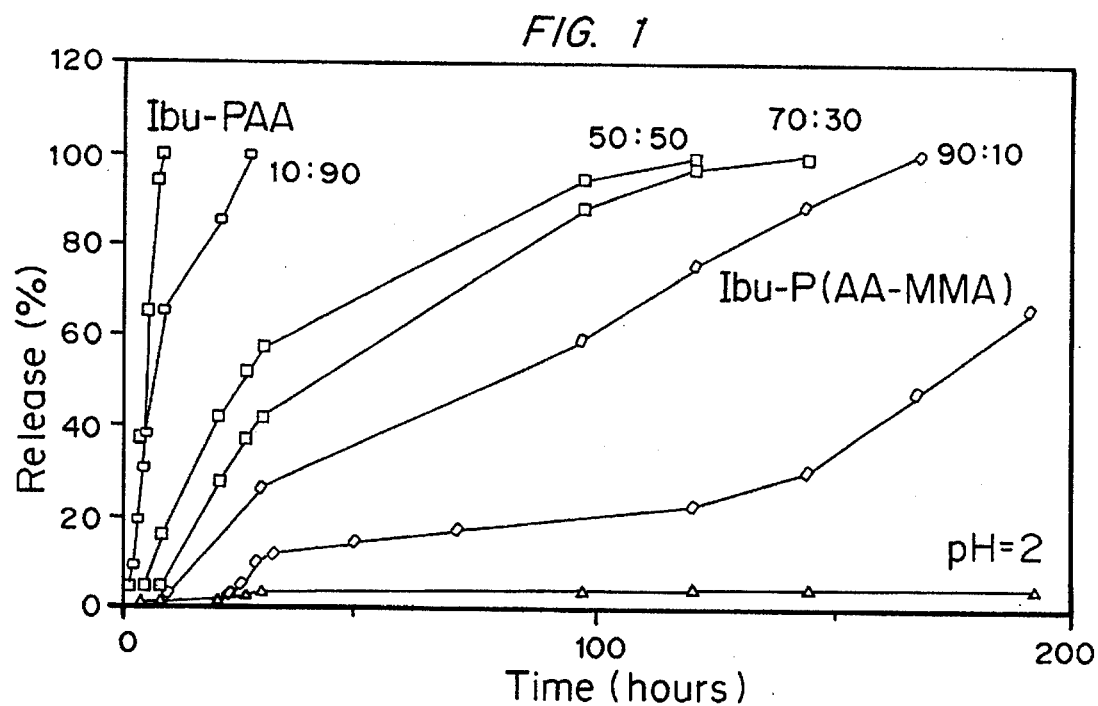
FIG. 1 is a graph illustrating the percent release of ibuprofen over time in hours from poly(acrylic acid) ibuprofen anhydride (open squares); poly(acrylic acid-methylmethacrylate) ibuprofen anhydride (open diamond); 10:90 poly(acrylic acid) ibuprofen anhydride/poly(acrylic acid-methylmethacrylate) ibuprofen anhydride; 50:50 poly (acrylic acid) ibuprofen anhydride/poly(acrylic acid-methylmethacrylate) ibuprofen anhydride; 70:30 poly (acrylic acid) ibuprofen anhydride/poly(acrylic acid-methylmethacrylate) ibuprofen anhydride; and 90:10 poly (acrylic acid) ibuprofen anhydride/poly(acrylic acid-methylmethacrylate) ibuprofen anhydride. The poly(acrylic acid) had a molecular weight of 2,000. The poly(acrylic acid-methylmethacrylate) was Eudragit L (MW 125,000). The experiment was conducted at pH 7.4 and pH 2 for the 50:50 mixture at 37° C., and monitored by UV at 265 nm.

Long acting absorbable ocular inserts for the delivery of substances to the eye are disclosed, in which the polymer carrier is eliminated simultaneously or approximately concurrently with drug release.

The inserts can be designed to release substances for any desired period including from one to seven days, after a single administration, without the need for the removal of the device after the drug has been released.

I. Definitions

The term (meth)acrylic refers to methacrylic or acrylic or mixtures thereof.

The term (meth)acrylate refers to methacrylate or acrylate or mixtures thereof. In one embodiment, (meth)acrylate is the $C_1$ to $C_{22}$ alkyl or alkenyl ester, including the methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl) or fatty acid esters.

The tern biologically active molecule or material as used herein refers to an organic molecule including a drug, a protein, polysaccharide, nucleoprotein, lipoprotein, synthetic polypeptide, or a small molecule linked to a protein, carbohydrate, glycoprotein, steroid, nucleic acid, nucleotide, nucleoside, oligonucleotides (including antisense oligonucleotides), cDNA, nucleic acids, genes, vitamins, including vitamin C and vitamin E, lipid, or combination thereof, that causes a biological effect when administered in vivo to an animal, including but not limited to birds and mammals, including humans. The term drug, as used herein, refers to any substance used internally or externally as a medicine for the treatment, cure, or prevention of a disease or disorder, and include but are not limited to immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, and radiation absorbers, including UV-absorbers.

The term biodegradable or bioerodible, as used herein, refers to a polymer that dissolves or degrades within a period that is acceptable in the desired application (usually in vivo therapy), usually less than one year, and preferably less than one month, on exposure to a physiological solution of pH 6–8 having a temperature of between 25° and 37° C. In a preferred embodiment, the device degrades in a period of between 1 hour and several weeks, according to the application.

The term hydrophobic refers to a material that absorbs water in a maximum amount not exceeding approximately 10 percent of its dry weight. A hydrophilic material is one that is not hydrophobic.

The term fatty acid refers to a alkanoic acid or alkenoic acid of $C_8$ to $C_{22}$, including but not limited to caproic, caprylic, capric, lauric, myristic, palmitic, stearic, arachidic, behenic, lignoceric, heptanoic, nonanoic, undecanoic, tridecanoic, pentadecanoic, heptadecanoic, nonadecanoic, heneicosanoic, tricosanoic, arachidonic, docosahexanoic, elaidic, erucic, linoleic, linolenic, nervonic, oleic, palmitoleic and petriselinic acids.

II. Substances to be Delivered

Any biologically acceptable substance, including a biologically active material, can be delivered using these methods and compositions. If the substance contains a carboxylic acid group, embodiments A, B or C can be used. If, alternatively, the substance does not contain a carboxylic acid group, embodiment B should be selected.

In embodiments A and C, the carboxylic acid groups on the polymer can be either partially or completely reacted with the substance to be delivered to form anhydride or methylene diester bonds, respectively. The more carboxylic acid groups that are initially bound to the substance, the more hydrophobic the polymeric insert will be, and therefore, the longer the insert will remain intact in the eye. In a typical embodiment, between 2 and 100 percent, and more typically, between 10 and 60 percent, of carboxylic acid groups are initially bound to the substance.

Nonlimiting examples of carboxylic acid-containing bioactive compounds are described, for example, in *The Merck Index*, 14th edition, (Merck & Co., Inc. New Jersey, 1989). Preferred substances are ibuprofen (a nonsteroidal anti-inflammatory) and ofloxacin (a fluoroquinolone antibiotic). Other examples include, but are not limited to, other nonsteroidal anti-inflammatory agents such as acetylsalicylic acid (aspirin); salicylic acid; sulindac; indomethacin; naproxene; fenoprofen; ketoprofen; diflunisal; tolmetin; flurbiprofen; mefenamic acid; suprofen; and tolfenamic acid; cephalosporin antibiotics such as cefametazole; cefazolin; cephalexin; cefaclor; cefuroxime; cefamadole, and cefoxitin; penicillin antibiotics such as benzylpenicillin; phenoxymethylpenicillin; ampicillin; carbenicillin; aziocillin; and piperacillin; steroidal monocarboxylic acids such as 6a-fluoro-11b-hydroxy-16a-methyl-3,20dioxopregna-1,4-dien-21-oic acid; 6a-fluoro-11b, 17a-dihydroxy-16b-methyl-3,20-dioxopregna-1,4-dien-21-oic acid; and 6a-fluoro-lib, 17a-dihydroxy-16b-methyl-3,20-dioxopregna-1,4-dien-21-oic acid; prostaglandins such as prostaglandin E2; prostaglandin E1; prostaglandin F2a; prostacyclin; ambaprostil; nileprost; and ciprostene; and angiotensin-converting enzyme inhibitors such as enalaprilic acid; captopril; N-cyclopentyl-N-[3-[2,2-dimethyl-1-oxopropyl)thio]-2-methyl-1-oxopropyl]glycine; 1-[4-carboxy-2-methyl-2R,4R-pentanoyl]-2,3-dihydro-2S-indole-2-carboxylic acid; lisinopril; tiopronin; and pivopril.

Other bioactive carboxylic acid-containing compounds, such as ethacrynic acid; methyldopa; 5-aminosalicylic acid; L-dopa; carbidopa; valproic acid; 5-hydantoinacetic acid; tranexamic acid; furosemide; methotrexate; chlorambucil; clofibric acid; amphotericin B; 6-aminocaproic acid; mecillinam; tretioin; 4-aminomethylbenzoic acid; mycophenolic acid; D,L-2,4-dihydroxyphenylalanine; all-trans-retinoic acid; 13-cis-retinoic acid; folic acid; cromoglycic acid; and nicotinic acid can also be delivered using this invention.

Bioactive compounds, regardless of whether or not they contain a carboxylic acid group, can be incorporated in poly(meth)acrylate anhydride or alkyl polymethacrylate anhydride matrices.

In particular, any drug used to treat the eye and surrounding tissues can be incorporated in the ocular insert of this invention. It may also be practical to use the eye and surrounding tissues as a point of entry for systemic drugs or antigens that ultimately enter circulation in the blood stream, or enter the nasopharyngeal area by normal routes, and produce a pharmacological response at a site remote from the point of application of the ocular insert. Thus, drug or antigens which will pass through the eye or the tissue surrounding the eye to the blood stream or to the nasalpharyngeal, esophageal or gastrointestinal areas, but which are not used in therapy of the eye itself, can be incorporated in the ocular insert.

Suitable drugs for use in therapy of the eye with the ocular insert of this invention are without limitation antibiotics such as tetracycline, chlortetracycline, bacitracin, neomycin, polymyxin, gramicidin, oxytetracycline, chloramphenicol, gentamycin, and erythromycin, antibacterials such as sulfonamides, sulfamothazole and sulfisoxazole; antivirals including idoxuridine, and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, prednisolone 21-phosphate, prednisolone acetate, fluoromethalone, betamethasone and triamcinolone; decongestants such as phenylephrine, naphazoline, and tetrahydrozoline; miotics and anticholinesterases such as pilocarpine, eserine salicylate, carbachol, diisopropyl fluorophosphate, phospholine iodide, and demecarium bromide, mydriatics such as atropine sulfate, cyclopentolate, homatropine, scopolamine, tropicamide, eucatropine, and hydroxyamphetamine; sympathomimetics such as epinephrine; peroxicam, 5-fluorouracil, methotrexate and other antiproliferative agents; pilocarpine, β-blockers such as timolol and metoprolol, dapiprazole, imirestate, falintolol, fusidic acid, suprofen, seftazidime, diclofenac, flurbiprofen, cefamandole, phenylephrine, lincomycin, acetbutolol, cefsulodin, methazolamide, cefotaxime, bufuralol, pyrilamide, and clonidine.

Drugs can be in various forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary x-onium salts) can be employed. Furthermore, simple derivatives of the drugs such as ethers, esters, amides, etc., which have desirable characteristics, but which are easily hydrolyzed by body pH, enzymes, etc., can be employed.

Ocular devices comprising the hydrophobic poly (carboxylic acids) of this invention may be used to deliver drugs which are substantially insoluble in water as well as those which are essentially water soluble. If it is necessary for the substance to remain in the eye for an extended period, the drug or substance should not be highly water soluble.

In accord with this invention, the ocular insert is intended to provide a complete dosage regimen for eye therapy over this prolonged period. Therefore, the amount of drug to be incorporated in the device is determined by the fact that sufficient amounts of drug must be present to maintain the desired dosage level over the therapeutic treatment period. The exact amount will depend upon the drug used and treatment period.

III. Embodiment A

In embodiment A of the invention, the insert and method include the covalent attachment of a carboxylic acid-containing substance to a polymer that contains pendent carboxylic acid groups, through anhydride linkages. The drug is released over time by hydrolysis of the anhydride bonds. The polymer-substance anhydride is initially hydrophobic. As the substance is hydrolysed from the polymeric backbone, the polymer is converted to a polycarboxylic acid that is hydrophilic and which is removed from the eye through the tearing process. Any pharmaceutically acceptable polymer that has carboxylic acid substituent groups can be used to prepare the anhydride. Suitable polycarboxylic acids include but are not limited to poly(methacrylic acid—methylmethacrylate) copolymers (Eudragit) and poly (acrylic acids) (PAA), which are commercially available in various molecular weights. Other polycarboxylic acids include the polymers or copolymers of crotonic acid or maleic acid, as well as those described in U.S. Pat. No. 3,811,444.

A preferred method of forming an anhydride bond between a carboxylic acid-containing bioactive compound and a polyacid involves anhydride exchange. The polycarboxylic acid and the carboxylic acid-containing substance is prepared by heating the two materials separately with acetic anhydride to form the corresponding mixed acetic acid anhydrides. These precursor anhydrides are then mixed and heated neat under vacuum to form the final product. Acetic acid is stripped off during the condensation process.

Other methods for synthesizing anhydrides are well known. See, for example, *The Chemistry of Acid Derivatives*, S. Patai ed. pt. 1, (Wiley, New York 1979); and *Basic Principles of Organic Chemistry*, J. D. Roberts and M. C. Caserio editors, (W. A. Benjamin, California, 1965). Anhydrides can be formed, for example, from two carboxylic acid molecules using a dehydrating agent. Common dehydrating agents are acetic anhydride, phosgene, diphosgene, triphosgene, dicyclohexylcarbodiimide, and methoxyacetylene. However, since these methods form symmetric anhydrides as well as the desired mixed anhydrides, this method is not preferred for preparing highly pure mixed anhydrides. A preferred method for forming mixed anhydrides of high purity without further isolation and purification is by reacting an activated carboxylic acid derivative with a carboxylic acid or the salt thereof.

Carboxyl groups on either the polyacid (polyanhydride precursor) or on the carboxylic acid-containing biologically active compound(s) can be activated in order to form an anhydride bond. Methods for activating a carboxyl group vary from traditional methods such as intermediate acid halide and acyl azide formation to more sophisticated methods, as described in detail in Larock, "Comprehensive Organic Transformation," VCH, New York (1989), hereby incorporated by reference.

A representative method for preparing acid chlorides is to react a carboxylic acid with thionyl chloride, preferably in benzene or toluene with a catalytic amount of dimethyl formamide. The resulting acid chloride can then be reacted with a carboxylate salt to form an anhydride.

Other reagents which can be used for carboxyl activation, under specified conditions, include pentafluorophenyl esters (Schon, I. and Kisfaludy, L., Synthesis, 303–305 (1986)) and 1-oxodihydrobenzotriazinyl(Dhbt) esters (Atherton, E., et al., J. Chem. Soc., Perkin Trans. 1, 2887–2894 (1988); Rivaille, P., Gautron, J. P., Castro, B. and Milhaud, G., Tetrahedron, 36, 3413–3419 (1980); Knorr, R., et al., Tetrahedron Lett., 30, 1927–1930 (1989)), the teachings of which are hereby incorporated by reference.

Benzotriazol-1-yl derivatives such as 2-(1H-Benzotriazol-1-yl)-1,1,3,3-tetramethyluronium tetrafluoroborate are preferred to DCC to minimize racemization, if chiral intermediates are used, and also to increase the reaction kinetics, as described in Reid, G. E. and Simpson, R. J., Ann. Biochem., 200, 301-309 (1992), hereby incorporated by reference. Active esters are a preferred activated carboxylic acid derivative, since they can normally be prepared in advance, stored for reasonable lengths of time without decomposition, typically six months, and provide good products yields, typically above 80%, in acceptable reaction times, for example, between two and 24 hours.

Reactions of carboxylic acid derivatives with unactivated carboxylic acid groups must be carried out with aprotic solvents, to avoid reacting the derivative with the solvent. Preferred solvents include dialkyl formamides, such as dimethylformamide, dialkyl sulfoxides, such as dimethylsulfoxide, aromatic solvents such as benzene, toluene, and xylenes, chlorinated solvents such as dichloromethane, chloroform, and trichloroethane, and ethers such as tetrahydrofuran and dibutyl ether. It is often preferred to use stoichiometric amounts of trialkyl amines, pyridine, or other aprotic bases as acid scavengers.

IV. Embodiment B

In embodiment B of the invention, a substance to be delivered (whether or not it contains a carboxylic acid group) is dispersed within a poly(meth)acrylate anhydride matrix, and the mixture is formed into an appropriately shaped article for ocular delivery. The substance is released over time, and the poly(meth)acrylate anhydride is simultaneously hydrolysed to a poly(meth)acrylic acid, which is removed from the eye in the tearing process. The substances to be incorporated should not chemically interact with the polymer during fabrication, or during the release process.

Poly(methacrylate anhydride) matrices containing ofloxacin casting, in which the polymer is dissolved in a solvent, and the substance to be delivered dissolved or dispersed in the solution. The solvent is then evaporated, leaving the substance in the polymeric matrix. Solvent casting requires that the polymer be soluble in organic solvents.

V. Embodiment C

In embodiment C of the invention, the insert and method include the covalent attachment of a carboxylic acid-containing substance to be delivered to a polymer that contains pendent carboxylic acid groups through methylene diestar bonds which hydrolytically degrade over time.

Methylene diestar bonds hydrolyze in water to the carboxylic acids. Methylene diestar bonds are more stable to hydrolysis than anhydride bonds, and are less stable to hydrolysis than α-hydroxy esters, i.e., polylactide. Since methylene diestar bonds are less sensitive to hydrolysis than the anhydrides of embodiments A and B, ocular inserts prepared according to embodiment C do not require the extensive storage conditions (under argon, under freezing temperatures) that may be required of the ocular inserts of embodiments A and B. For ocular inserts in which a longer release duration, for example, between several days and several weeks, and long shelf-life under simple storage conditions, ocular inserts prepared according to embodiment C are preferred.

Methods for preparing hydrolyzable methylene diestar polymeric prodrugs include those methods described for preparing ofloxacin ester prodrugs [M. Ertain, E. Palaska, R. Ertan, and N. Yulug, Arzneimittel-Forschung/Drug Research 42(1), 1, 70–72 (1992); and Y. Meada, K. Omoda, et el. Biol. Pharm. Bull. 16(6) 594–599 (1993)), the contents of which are hereby incorporated by reference.

Ofloxacin binding to polyacrylic acid via methylene diester bond

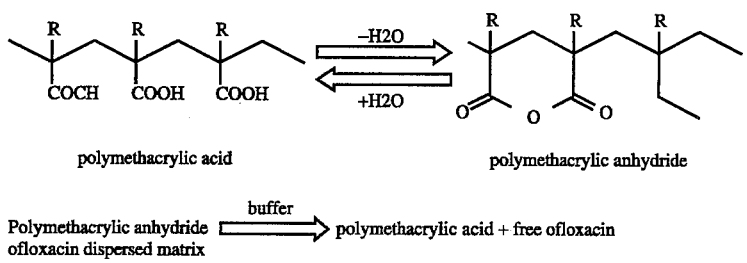

polymethacrylic acid     polymethacrylic anhydride

Polymethacrylic anhydride ofloxacin dispersed matrix $\xrightarrow{\text{buffer}}$ polymethacrylic acid + free ofloxacin R=ofloxacin The polymer must have enough of its carboxylic acid groups converted to anhydrides to render the polymer sufficiently hydrophobic that it retains its integrity for a suitable time when placed in an aqueous environment, such as the body, and stable enough to be stored for an extended period before use. The polymer must be strong, yet flexible enough that it does not crumble or fragment during use.

In a typically embodiment, between 2 and 100 percent, and more typically, between 10 and 60 percent, of the carboxylic acid groups are converted to internal anhydrides.

Loaded controlled release devices are typically prepared in one of several ways. The polymer can be melted, mixed with the substance to be delivered, and then solidified by cooling. Melt fabrication requires that the polymer have a melting point that is below the temperature at which the substance to be delivered and polymer degrade or become reactive. Alternatively, the device can be prepared by solvent

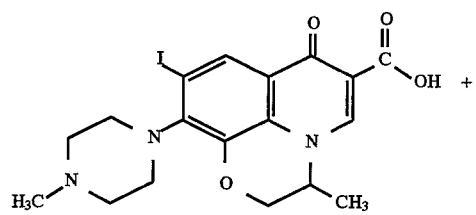

-continued

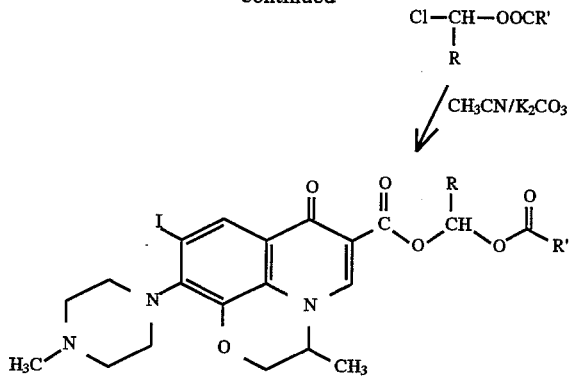

R=H, CH3
R'=poly(acrylic acid), poly(methacrylic acid-methylmethacrylate)

In one embodiment, the carboxylic acid containing substance is reacted with a halomethyl ester, for example, $[Cl(R)CHO(O)C]_nR'$, wherein R is H or $C_{1-5}$ alkyl, and preferably $CH_3$, R' is the residue of the carboxylic acid containing polymer, and n is the number of carboxylic acid groups on the polymer to be converted to methylene diester linkages. In another embodiment, the polycarboxylic acid is reacted with a halomethyl ester such as Cl(R)CHO(O)CR", wherein R is H or $C_{1-5}$ alkyl, and preferably $CH_3$, and R" is the residue of the carboxylic acid containing substance to be delivered.

VI. Preparation of Ocular Insert

The polymeric materials of embodiments A, B, and C, can be used as is to form ocular inserts, or, alternatively, can be mixed with other polymers or additives to modify the properties of the device, including hydrophobicity and drug release rate. Nonlimiting examples of other polymers that can be included are biodegradable, biocompatible polymers, such as polyglycolic acid, collagen, polyorthoesters, polylactic acid, cellulose ester derivatives, dextran and its derivatives, albumin, gelatin, hyaluronic acid, amylose and its derivatives, poly(vinyl alcohol), maleic anhydride derivatives, and polyphosphazenes.

The insert can be in any shape that is suitable for application to the eye. These shapes include, but are not limited to, ellipsoid, bean, banana, circular, rectangular, doughnut, crescent and half-circle devices. The devices can be doubly convex, concave-convex or rectangular, and, since the films are flexible, they will generally tend to conform to the shape of the eye. Preferably, the insert is transparent and clear to minimize visual impairment. Alternatively, the insert can contain a UV blocking compound and/or can be colored, to provide protection from light. This embodiment is especially important when the eye of a patient in need of an ocular polymeric delivery device has become sensitive to light. The dimensions of the device, the thickness and size of the device, and the amount of substance such as the biologically active material in the device, can vary widely as desired. Typically, the thickness and size of the insert varies between approximately 0.01 and 2 mm and 5 and 100 $mm^2$, respectively. Typically, the amount of compound that is in the insert is preferably between approximately 0.5 and 500 mg.

The drug release rate and total elimination time of the device from the eye is controlled by, among other factors, the degree of drug attachment or dispersement (loading) on the polymer, the molecular weight, the hydrophilicity and rate of hydrolysis of the polymer carrier, the additives, if any, in the film, and the size and consistency (density) of the device.

It is often desired to incorporate plasticizers in the device to improve or vary its physical properties, such as to make it more flexible. Examples of plasticizers are the pharmaceutically acceptable plasticizers conventionally used, such as acetyl tri-n-butyl citrate, polyethylene glycol (600), epoxidized soybean oil, glycerol monoacetate, polyethylene glycol, propylene glycol dilaurate, decanol, dodecanol, 2-ethyl hexanol, 2,2-butoxyethanol and the like. The proportion and selection of plasticizer used will vary within broad limits depending upon the characteristics of the polymeric system used.

When plasticizers are included in the poly(carboxylic acid) materials they are typically added prior to shaping the final formed structure, such as by dissolving or dispersing then in the solution from which the film is cast.

Solutions of the polymeric materials of embodiments A or C can be placed in a solvent such as dichloromethane and cast on Teflon coated glass at room temperature. A film is formed as the solvent evaporates. The film thickness is determined by the amount of solution cast per unit area. Drug-loaded polymeric matrices of embodiment B can be prepared in a similar fashion by adding one or more biologically active compounds, in solution or suspension, to a polyanhydride solution prior to casting. A preferred concentration of the compounds is between approximately 5 and 40 weight percent of the dry weight of polymer.

The ocular inserts can be suitably packaged using a drug and moisture impermeable packaging material such as the foil-polylaminates, e.g., aluminum foil-polyethylene laminate or aluminum foil-polyester (Mylar)-laminate. The ocular devices are preferable sterilized prior to insertion in the eye. The sterilization can be effected prior to packaging or after packaging using any appropriate method, for example, radiation or exposure to ethylene oxide. See, generally, *Remington's Pharmaceutical Sciences*, Vol- XIV, 1970, pp. 1,501–1,518.

The rate of bioerosion and drug release of materials employed in the invention can be determined experimentally by evaluation under simulated ocular environmental conditions. For example, the rate of ocular bioerosion of a material may be measured by placing a small weighed sample of the material in a 0.026M $HCO_3$-solution of pH about 7.4 (simulated tear fluids) at body temperature (37° C.), agitating for a timed interval, and periodically measuring the amount of material eroded into the solution. To accurately predict in vivo results, it is necessary to multiply the in vitro rates by an experimentally determined constant which takes into account differences in stirring rate and eye fluid volumes between the eye and the in vitro test apparatus. This constant may be derived by first placing a plurality of small weighed samples of material in a plurality of eyes and sequentially, over a period of time, removing and weighing the samples. The rate thus determined, divided by the rate of erosion observed in vitro with the same, material, equals the necessary constant.

VII. Other Delivery Devices

The polymeric materials disclosed herein can also be used as coatings for implantable devices, i.e., stents, catheters, artificial vascular grafts, and pacemakers, for oral drug administration such as compressed tablets or coatings of tablets for oral controlled drug delivery, as well as for nonmedical applications, including the controlled release of insecticides and fungicides. The polymeric materials can also be made into microspheres or nanospheres for the controlled delivery of substances.

As used herein, the term nanoparticle refers to a solid particle of size ranging from 10 to 1000 nm. The 'ideal' nanoparticle is biodegradable, biocompatible, has a size of less than 200 nm and has a rigid biodegradable core that has incorporated in it the substance to be delivered. The term "microparticle," as used herein, refers to a particle of size ranging from greater than one micron to 1000 microns. Any of the nanoparticles described herein can be alternatively fabricated as microparticles if more appropriate for the desired application. Microparticles and nanoparticles can be prepared using any of a number of known procedures.

VIII. Examples

The methods and compositions of the present invention will be further understood with reference to the following non-limiting examples.

Materials

Acrylic acid, ibuprofen and poly(acrylic acid) (MW 2,000) and (MW 5,000) were purchased from Aldrich. Poly(methacrylic acid-methylmethacrylate) (Eudragit L) was provided by Rhom Pharma (Germany). Thionyl chloride, oxalyl chloride, and acetic anhydride were freshly distilled under nitrogen prior to use. All solvents were analytical grade.

Instrumentation

Infrared (IR) spectroscopy (Anelect Instruments FT-IR model fx-6160) was performed on drugs and polymer samples cast on NaCl plates from solutions in $CH_2Cl_2$. Ultraviolet (UV) spectroscopy was performed using a Kontron Instruments Uvikon model 930. $^1H$ NMR spectra ($CDCl_3$/TMS/d/ppm) were obtained on a Varian 300 MHz spectrometer. High Pressure Liquid Chromatography (HPLC) and GPC apparatus: a Spectra Physics (Darmstadt, Germany) modular system composed of a Spec1000 pump, a UV-detector and a Data Jet integrator. A Rheodyne (Cotati, Calif.) injection valve equipped with a 20 mL loop was used. The pH was measured on a PHM62 standard pH meter (Radiometer, Copenhagen). Molecular weights of the polymers were estimated on a gel permeation chromatography (GPC) with UV at 254 nm. Samples were eluted with $CHCl_3$ through a linear Styrogel column (Waters) at a flow rate of 1 mL/minute using chloroform as mobile phase. The molecular weights were estimated relative to polystyrene standards (Polyscience, Warrington, Pa.) with a molecular weight range of 400 to 1,500,000 using a WINner/286 computer program.

Ofloxacin Analysis

Ofloxacin was determined using a published HPLC method (Maeda, Y., Biol. Pharm. Bull. 16(6) 594–599, 1993] using a mixture of acetonitrile: 0.01M $KH_2PO_4$: triethylamine (140:860:2 v/v/v). The pH was adjusted to 2.8 with formic acid. A C18 Lichospher 100 column (Merck, Dorstadt, Germany, cat. no. 50833, 250×4 mm, 5 microns) at a flow rate of 1 mL/minute was used. Ofloxacin was detected by UV at 303 nm. Typical retention time for ofloxacin was 3.8 minutes.

TLC analysis was determined on silica gel plates using a mixture of dichloromethane:methanol: water at 18:6:0.5 v/v ratio. Ofloxacin spots were recognized under UV light at 254 nm (Rf=0.43). Quantitative analysis of ofloxacin in buffer solutions was determined by UV at 303 nm.

Ibuprofen Analysis

Quantitative analysis of ibuprofen was obtained using HPLC or UV at 270 nm. HPLC conditions: C18 Lichospher 100 column (Merck, Dorstadt, Germany, cat. no. 50833, 250×4 mm, 5 microns) using a 70:30 acetonitrile:water as mobile phase at a flow rate of 1 mL/minute were used. Ibuprofen was detected by UV at 270 nm. A typical retention time was 4.4 min.

EXAMPLE 1

Preparation of Ibuprofen Acid Chloride

Ibuprofen was dissolved in thionyl chloride (2 grams in 5 ml) and refluxed for 2 hours. After distilling off the thionyl chloride using an oil pump (170° C., 0.5 mm Hg) the crude yellow liquid was extracted with hexane (90% yield). IR (film cast) 1800 cm-1 (Cl—C=O) H NMR: 7.22 (q, 4H); 4.12 (q, 1H); 2.53 (D, 2H); 1.88 (Octa, 1H); 1.62 (D, 3H); and 0.95 ppm (D, 6H).

EXAMPLE 2

Preparation of Polymer-Acid Chloride

Poly(acryloyl chloride) and poly(MMA-MA)1:1 acid chloride (Eudragit L-Cl) were prepared as follows. Poly (acrylic acid) (MW 2,000) was reacted with excess thionyl chloride (10 grams with 50 grams thionyl chloride) under reflux for 5 hours. Excess thionyl chloride was removed by evaporation and the resulting polymer was purified by precipitation in diethyl ether from a chloroform solution. The polymer contained 20–22% chloride which accounts for about 50% conversion to the acid chloride groups. The acid chloride derivative of poly(MMA-MA)1:1 (Eudragit L) was prepared similarly from the reaction with thionyl chloride. Elemental analysis indicated between 15 and 18 percent chloride which accounts for about 50% conversion to acid chloride groups. The IR showed typical acid chloride peaks at 800, and 1804 $cm^{-1}$ (in addition to 1710–1730 $cm^{-1}$ for the acid and ester groups. $^1H$ NMR ($CDCl_3$, TMS) was similar to the acid with some minor chemical shifts.

EXAMPLE 3

Preparation of Poly(Acrylic Anhydride)

PAA (MW 2,000, 10 grams) was added to refluxing acetic anhydride (100 ml) and the reaction mixture was heated for one hour. The resulting clear solution was filtered through to remove insoluble solids and the filtrate was evaporated to dryness. The white solid residue was purified by precipitation (diethyl ether/dichloromethane) to yield 9.5 grams of a white powder IR-1740, 1802 $cm^{-1}$ Molecular weight (by GPC): Mw—2,300, Mn—1800. The product is soluble in dichloromethane, chloroform, THF, and ethyl acetate.

Eudragit L anhydride was prepared similarly. IR-1740, $1802^{-1}$, Molecular weight (by GPC): Mw—158,000.

EXAMPLE 4

Preparation of Eudragit L Anhydride Films

Solutions of Eudragit L anhydride in dichloromethane (10 wt %) were cast on Teflon coated glass at room temperature. The solvent was evaporated to yield a clear flexible film. The film thickness was determined by the amount of solution cast per unit area. Drug-loaded films were prepared by adding drugs, for example, ofloxacin or ibuprofen, in an amount between approximately 5 and 20 weight percent to the polymer solution prior to casting. Films containing various amounts of poly(acrylic anhydride) were prepared by mixing 10 weight percent solutions of Eudragit L and PAAn at various ratios prior to cast.

PAA of 2,000 molecular weight did not form a film by solvent casting and thus compressed tablets were prepared by mixing the drug and polymer powders (200 mg) and compressing them at 10,000 PSI using a Carver laboratory press.

EXAMPLE 5

Release Studies

Drug release studies were conducted by placing each polymer sample, films (100 mg, 20×30×0.15 mm) or tablets (200 mg, 14×0.1 mm) in 20 ml phosphate buffer 0.1 N pH 7.4 at 37° C. The drug concentration in the solution was determined by UV detection at 303 nm for ofloxacin and 270 nm for ibuprofen. The polymer dissolution was determined by weight loss.

EXAMPLE 6

Ibuprofen Conjugation to Polymers

The ibuprofen reaction product showed a significant peak (UV detection at 280 nm-ibuprofen absorption peak) at the polymer retention time (7–9 min) with a relatively small peak for unbound ibuprofen.

High binding yields were obtained in both methods, as shown below in Table I. Both ibuprofen and the polymers yielded the acid chloride derivatives as confirmed from the chloride analysis and IR absorption at 1800 cm$^{-1}$. $^{1}$H NMR spectra confirmed that the structures of the acid chlorides were similar to the respective acids and that these compounds did not degrade during the reaction.

TABLE 1

| Ibuprofen anhydride bound polyacrylate | | | |
|---|---|---|---|
| | | Yield | % Bound Drug |
| | MW | (%) | Method I | Method II |
| Ibuprofen | | | | |
| PAA | 2,000 | 85–90 | 50 ± 5 | 32 ± 7 |
| PAA | 5,000 | 75–85 | 30 ± 42 | 5 ± 5 |
| Eudragit L. | 125,000 | 75–85 | 10 ± 2 | 8 ± 2 | a. Drugs were conjugated from the anhydride interchange reaction (Method II) and from the Schotten Bowmann, acid-acid chloride, reaction (Method I). The bound drug was determined by hydrolysis of the product and determine the drug content in the hydrolysis solution by UV.
b. Drug binding yield was calculated as the percentage of polymer carboxylic acid side groups participated in drug binding.

The anhydride derivatives were prepared by reacting the acid chloride of a carboxylic acid containing bioactive compound with a polyacid (method 1) or by reacting a carboxylic acid containing bioactive compound with a polymer acid chloride (method 2). Ibuprofen binds in good yields to the polymer by both methods (10–50% binding per polymer carboxylic side groups).

EXAMPLE 7

Binding Ibuprofen Using the Reaction in Acetic Anhydride

Polymer conjugates of ibuprofen and poly(acrylic acid) Mn—2,000 or copoly(methacrylic acid: methylmethacrylate)1:1 (Eudragit L] were prepared by reacting the acetic acid mixed anhydrides of ibuprofen and the polymer.

Poly(acrylic acid) and ibuprofen were reacted separately with excess acetic anhydride to form corresponding acetic mixed anhydrides. The purified mixed anhydrides were reacted at 100° C. for 2 hours to yield a viscous liquid melt which solidified at room temperature to a transparent mass. The polymer-ibuprofen anhydride conjugate was purified from unbound ibuprofen by precipitating the polymer is diethyl ether from a dichloromethane solution. The polymer contained about 10 weight percent of bound ibuprofen.

Figure 2:
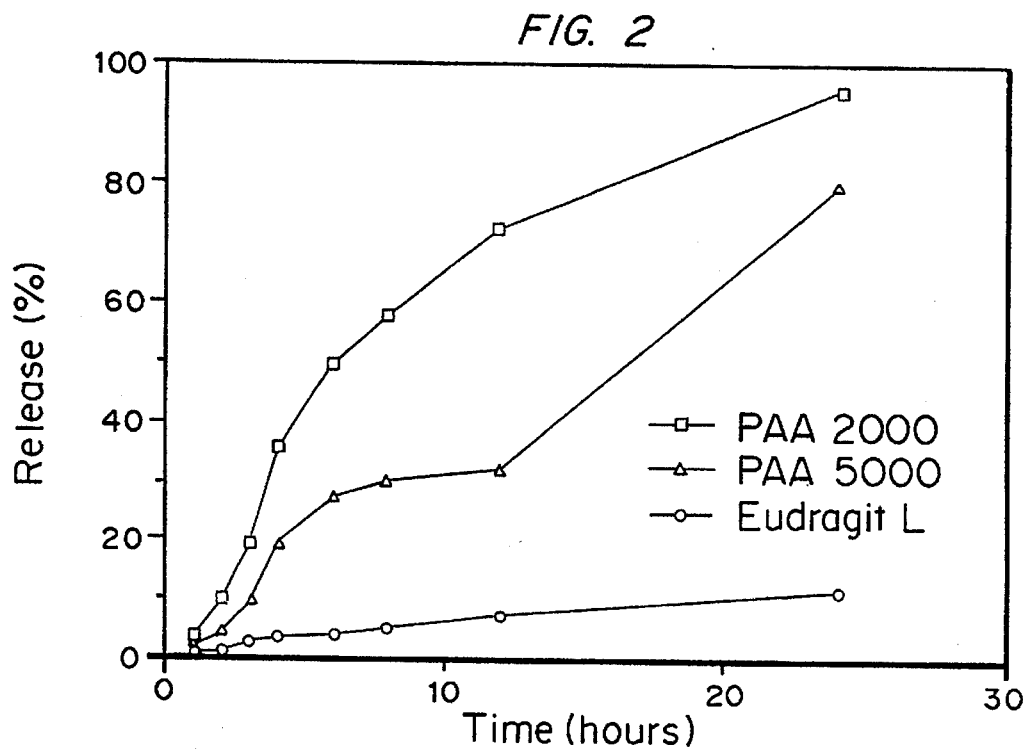
FIG. 2 is a graph illustrating the release of ibuprofen over time in hours from poly(acrylic acid) ibuprofen anhydride (PAA) (MW 2000, open square; NW 5000, open triangle) and Eudragit L at pH 7.4 at 37° C.
Figure 3:
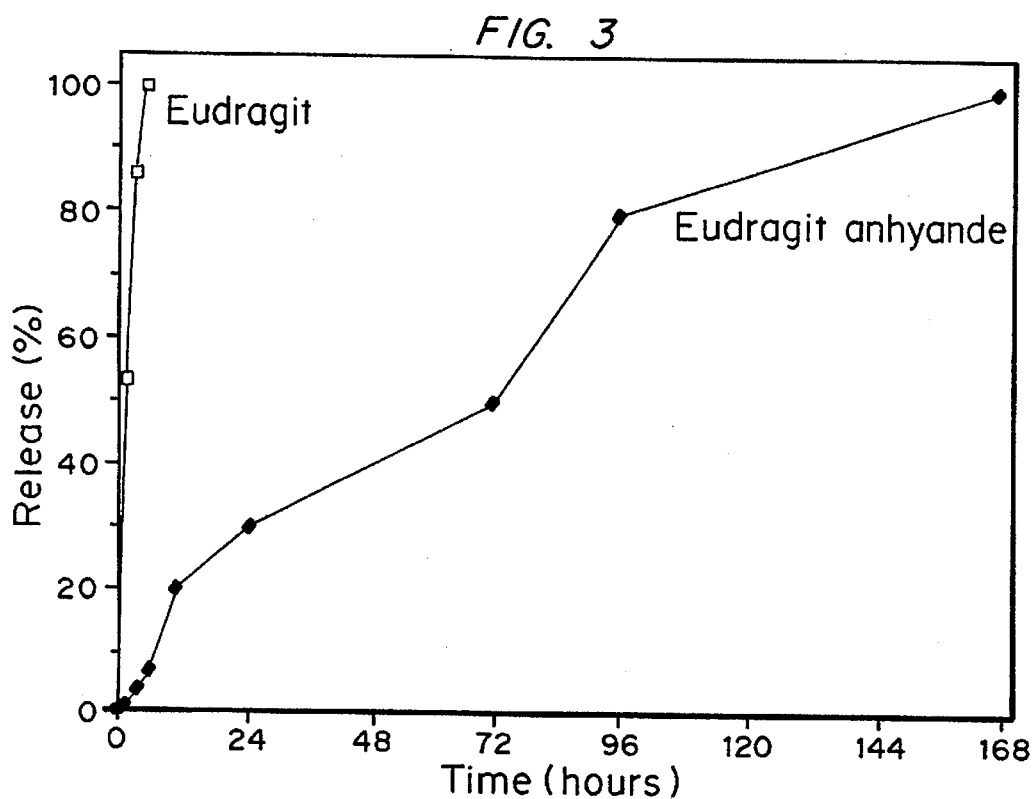
FIG. 3 is a graph illustrating the percent release of ofloxacin from polymer films loaded with ofloxacin. Films prepared from Eudragit L loaded with 10% ofloxacin added are represented by the open squares. Films prepared from Eudragit anhydride loaded with 10% ofloxacin are represented by the closed squares.

Flexible films were obtained by solvent or melt film formation techniques. The films were tested for ibuprofen release in buffer solution at 37° C. As seen in FIGS. 1 and 2, ibuprofen was released constantly for 1 to 7 days as a function of polymer molecular weight and hydrophobicity and polymer composition. The polymer was gradually eroded parallel to drug release and was completely eliminated in vitro shortly after all of the drug was released (FIG. 3).

EXAMPLE 8

Polyacrylate Anhydride Matrices Releasing Ofloxacin

Figure 4:
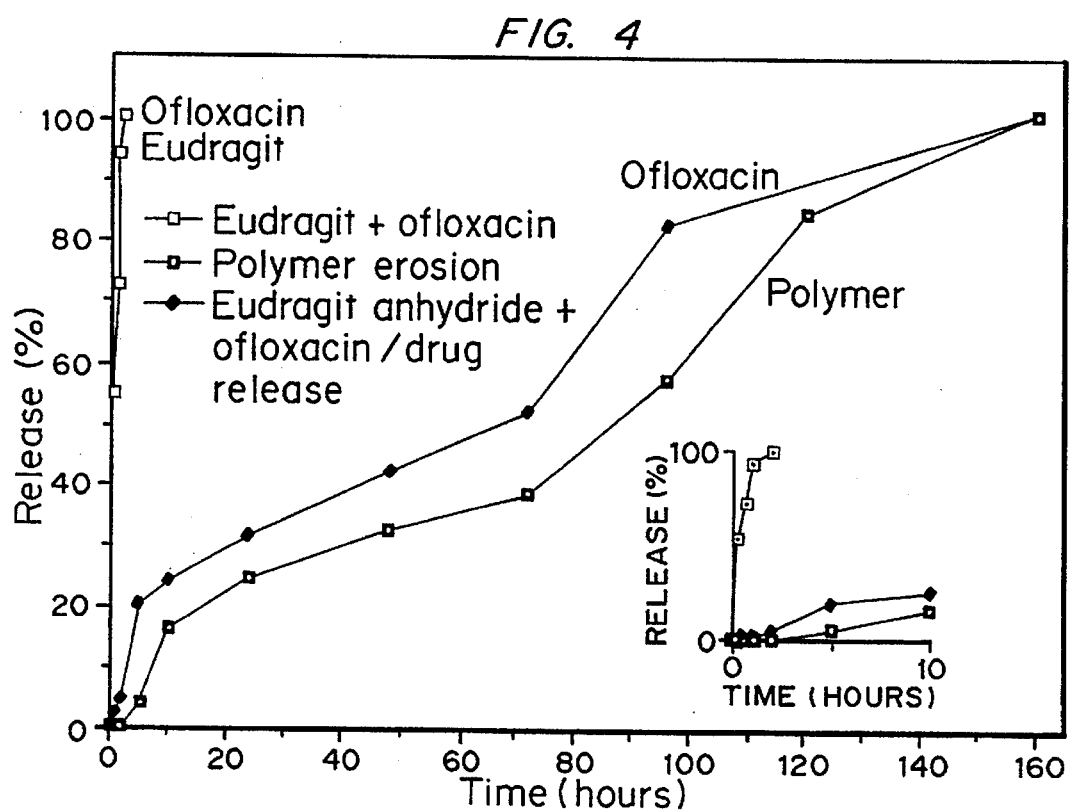
FIG. 4 is a graph illustrating the release and erosion of ofloxacin from matrices of untreated Eudragit L and Eudragit L anhydride; untreated Eudragit L (open square); ofloxacin release from Eudragit L anhydride (closed diamond) and polymer erosion (closed square). Matrices loaded with 10% by weight ofloxacin were placed in 0.1M phosphate buffer at pH 7.4. The release of ofloxacin was monitored by UV and the polymer erosion was monitored by measuring the weight loss with time.
Figure 5:
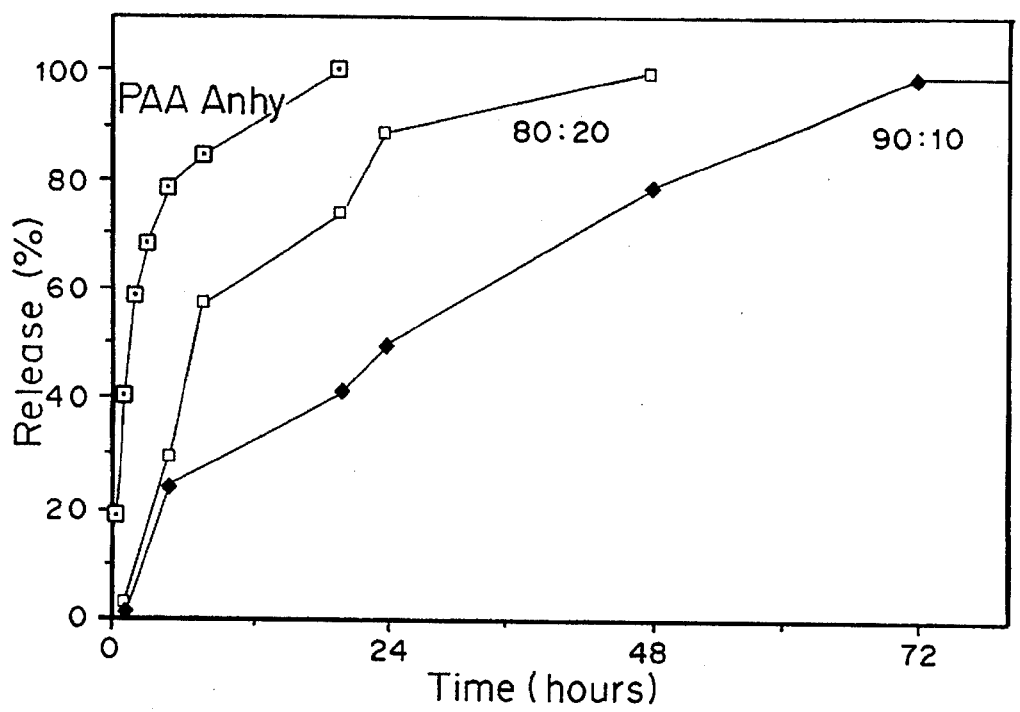
FIG. 5 is a graph illustrating the release over time in hours of ofloxacin dispersed in tablets of poly(acrylic anhydride) (PAAn) and Eudragit L anhydride (EUAn). 100% PAAn (open square); 90:10 mixture of PAAn and EUAn (closed square with open dot in the middle); 80:20 mixture of PAA and EUAn (closed square). Tablets (200 mg, 14×1 mm) were loaded with 10 weight percent ofloxacin, and the release was measured at pH 7.4 and 37° C.

Matrices of Eudragit anhydride and poly(acrylic anhydride) loaded with ofloxacin or ibuprofen were prepared as follows. PAA and Eudragit L were reacted with acetic anhydride to form the anhydride derivatives of the polymers. These anhydrides were soluble in chloroform and dichloromethane and formed flexible transparent films from solvent casting. For comparison, unreacted Eudragit L formed a brittle film from ethanol solution. Ofloxacin or ibuprofen loaded films were prepared by mixing the drug in the polymer solution and casting on a flat glass. Ofloxacin containing films (10 wt %) were opaque and flexible and released the drug for periods from 1 to 7 days as a function of polymer composition (FIGS. 4 and 5). During drug release the films were reduced in size but did not crumble. The polymer erosion was determined by sample weight loss followed the drug release pattern.

Figure 6:
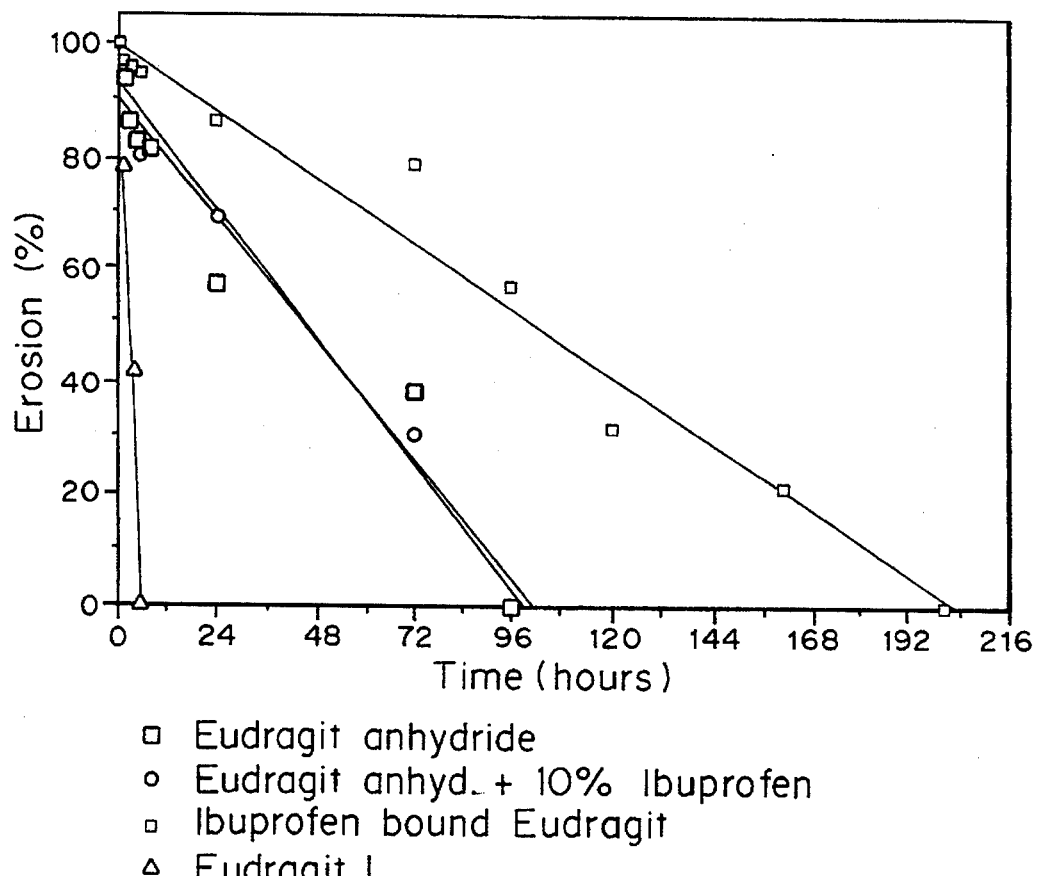
FIG. 6 is a graph illustrating the percent erosion rate of matrices of Eudragit L anhydride without drug (open squares); ibuprofen dispersed in Eudragit L anhydride matrices (open circle); ibuprofen bound Eugradit L anhydride (closed square); and untreated Eudragit L without or without ibuprofen (open triangle).

Ibuprofen was incorporated in polyacrylate anhydride matrices and drug release and polymer erosion was studied. Films loaded with 10 wt % ibuprofen were transparent and the release and erosion patterns were similar to that of ofloxacin (FIG. 6).

Adding plasticizers like polyethylene glycol —600 and tributyl citrate (5 wt %) to the polymer solution before casting increased film flexibility. Films with better flexibility were obtained particularly with tributyl citrate. Adding plasticizers did not significantly alter the drug release and polymer erosion patterns in vitro.

EXAMPLE 9

Ofloxacin and Ibuprofen Binding to Eudragit L via Methylene Diester Bond Formation The methods for preparing hydrolyzable methylene diester polymeric prodrugs were adopted from the methods described for preparing ofloxacin ester prodrugs (M. Ertain, E. Palaska, R. Ertan, and N. Yulug, Arzneimittal-Forschung/Drug Research 42(1), 1, 70–72 (1992); Y. Maeda, X. Omoda, et al. Biol. Pharm. Bull. 16(6) 594–599 (1993)].

The chloromethyl esters of Eudragit and PAA were prepared using the literature method for the preparation of chloromethyl pivalate (M. Roasmussen and N.J. Leonard, J. Amer. Chem. Soc. 89,5439, 1967), from the reaction with paraformaldehyde and zinc chloride. The Eudragit L chloromethyl ester derivative was reacted with ofloxacin as follows: Ofloxacin (722 mg, 2 mmol) was dissolved in acetonitrile and heated at 50° C. To this solution was added 200 mg (1.4 mmol) of anhydrous potassium carbonate and the reaction mixture was allowed to stir at 50° C. for 5 hours and 400 mg of Eudragit L chloromethyl ester was added. After 24 hours the reaction mixture was cooled to room temperature where 60 ml of water were added, followed by treatment with 1N NaOH. The mixture was extracted three times with chloroform and the chloroform was evaporated to dryness after it was washed with distilled water and dried over anhydrous MgSO4. The semisolid was redissolved in chloroform and precipitated in 1:1 ether hexane to yield a white precipitate (510 mg). NMR analysis confirmed a 14.5% by weight content of ofloxacin. Ofloxacin was released in phosphate buffer pH 7.4 at 37° C. for 15 days. The solutions collected from the in vitro degradation and release were effective in inhibiting Staphylococcus aureus when tested in agar plates, indicating the release of active drug. The same method was used to bind ibuprofen and mefenamic acid with a binding yield of 60 to 70%. Ibuprofen was released in vitro for 13 days from films (0.1 mm thick) made from ibuprofen bound Eudragit L (11% wt content). The structure of this conjugate is:

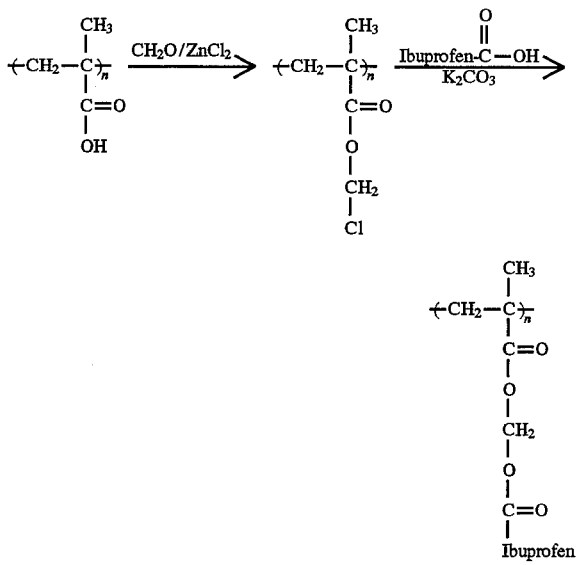

EXAMPLE 10

Preparation of Poly(malic acid) Based Anhydride Carriers

Anhydride carriers based on biodegradable poly(malic acid) were synthesized according to Guarin [Tetrahedron: asymmetry 4, 1925–1930, 1993; Polymer Bulletin, 14, 187–192, 1985; Makromol. Chem. Macromol. Symp. 6,305–314, 1986]. This polyester containing carboxylic acid side groups is water soluble and biodegrades in water into malic acid derivatives. In this invention, it was used as a carrier of drugs by attachment of a drug to its free carboxylic acid side groups via an anhydride bond. In addition, the polymer was converted into a biodegradable water insoluble polyanhydride carrier either by the formation of internal cyclic anhydrides or by coupling inert fatty acids to the carboxylic acid side groups by hydrolyzable anhydride bonds. In a typical experiment, poly(malic acid) was added to a dichloromethane solution containing ibuprofen chloride and crosslinked poly(4-vinyl pyridine) (PVP) as a proton acceptor. The reaction mixture was left to react in an ice bath for 24 hours. The amount of ibuprofen chloride was equal to 50 mole % of the carboxylic acid side groups in the polymer carrier. The PVP was isolated by filtration and the ibuprofen bound polymalic anhydride was isolated by precipitation in a 1:1 mixture of ether:petroleum ether. A white powder was obtained which 35% of the carboxylic acid groups bound ibuprofen, as determined by NMR. IR analysis of the polymer showed anhydride absorption at 1804 and 1742 cm–1, and ester absorption at 1720 cm–1. Ibuprofen release from compressed tablets (14×1 mm, 200 mg) in buffer pH 7.4 showed 50% and 100% ibuprofen release after 3 and 8 days at 37° C.

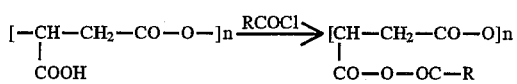

wherein R is a drug or fatty acid residue

EXAMPLE 11

Polymer Carriers Based on Crosslinked Polymethacrylic Acid Anhydride.

Crosslinked polymethacrylic acid, Carbopol 940, was reacted with refluxing acetic anhydride at a 1:10 w/v ratio for 1 hour. The insoluble anhydride polymer was isolated by filtration and purified by swirling in diethyl ether for 2 hours at room temperature. IR analysis indicated a full conversion into internal anhydride bonds.

The Carbopol anhydride (1 gram) was swelled for 3 hours in 5 mL of a dichloromethane solution containing dexamethasone (200 mg). The excess solution was isolated by decantation and the solvent was evaporated to dryness to yield a white powder loaded with dexamethasone. Dexamethasone was released constantly for 1 week from these particles when placed in buffer pH 7.4 containing 10% v/v of polyethylene glycol.

Carbopol anhydride was used for the anhydride conjugation of naproxene. Naproxene acetate anhydride was prepared from the reaction with acetic anhydride at reflux for 1 hour. Naproxene acetate anhydride was dissolved in dichloromethane (300 mg in 5 ml) and Carbopol anhydride (1.0 g) was added to the solution. After swelling for 5 hours the solvent was evaporated and heated at 150° C. for 1 hour under vacuum of 1 mm Hg. The resulting polymer was swirled in 20 ml dichloromethane for 1 hour, filtered and evaporated to dryness to yield a white powder of naproxene bound Carbopol.

EXAMPLE 12

Polymer Carriers Based on Poly(citryl acrylate anhydride)

Polymer carriers based on poly(citryl acrylate anhydride) were prepared as follows: Finely powdered citric acid was dispersed in dry dichloromethane containing an equimolar amount of PVP. To the stirred mixture in an ice bath was added dropwise a 10% solution of methacryloyl chloride (1 equivalent) for 2 hours. After stirring over night the mixture was filtered, the filtrate was evaporated to dryness, and the residue was swirled in water and extracted with dichloromethane. The water fraction was lyophilized to yield the citryl acrylate monomer. This monomer was polymerized or copolymerized with methacrylic acid or methylmethacrylate in water solution using a redox catalyst. The citryl methacrylate polymer was reacted with ibuprofen.

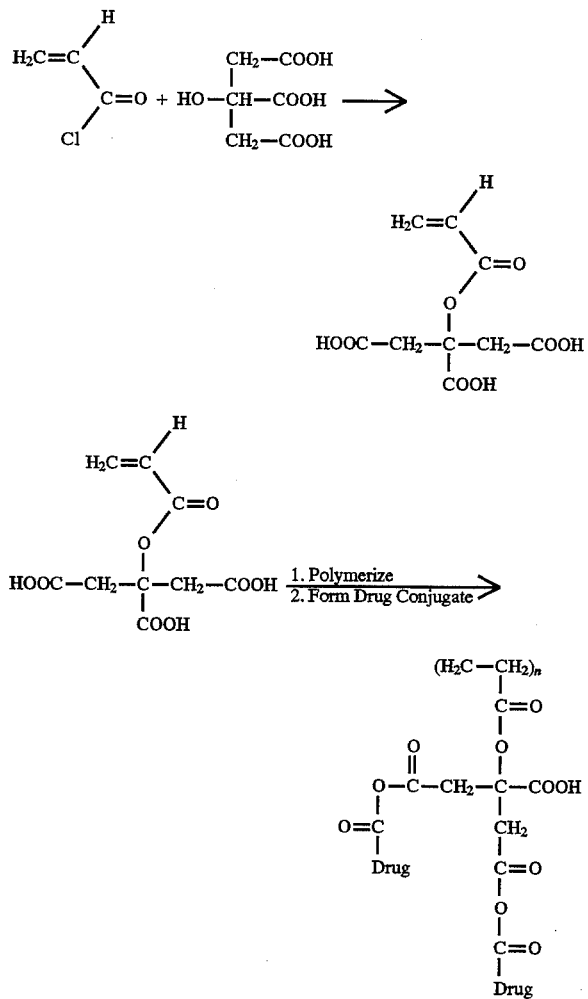

EXAMPLE 13

Polymer Carriers Based on Poly(stearyl methacrylate anhydride)

Poly(methacrylic acid) Mw=2000 was dissolved in a solution of acetic anhydride (1:10 w/v ratio) containing increasing amounts of stearic acid (from 10 mole % to 100 mole % based on the carboxylic acid units in the polymer). The mixture was allowed to reflux for 30 minutes and then evaporated to dryness. The residue was dissolved in dichloromethane and precipitated in diethyl ether. The purified polymer contained anhydrides and no carboxylic acid groups. The anhydrides were internal cyclic anhydrides and/or stearyl conjugated anhydrides. The hydrophobicity of the anhydride polymer derivatives was related to the stearyl content in the polymer. The more stearyl units attached to the polymer, the more hydrophobic the polymer is. The stearyl groups can be replaced by other fatty acids of various chain length such as dodecanoyl-, lauroyl-, and octanoyl- anhydride. Shorter chain length provided a faster degradation rate.

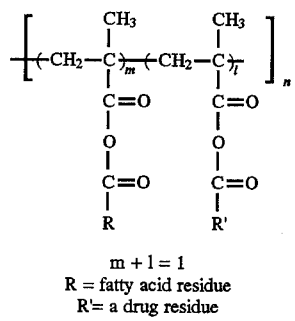

$m + 1 = 1$
R = fatty acid residue
R' = a drug residue

The experimental results demonstrate that attaching a prodrug such as ibuprofen to a water-soluble polymer provides an extended drug release at the same time the polymer carrier dissolves.

Modifications and variations of the present invention will be obvious to those skilled in the art from the foregoing detailed description of the invention. Such modifications and variations are intended to come within the scope of the appended claims.

I claim:

1. An ocular insert comprising a carboxylic acid-containing biologically active compound bound to a polyacid containing pendent carboxylic acid groups through an anhydride or methylene diester bond.

2. The insert of claim 1, wherein the polyacid is selected from the group consisting of polymers and copolymers of (meth)acrylic acid, maleic acid or vinylacetic acid.

3. The insert of claim 1, wherein the polyacid is an ester, partial ester, or anhydride of a polyacrylic acid with a compound containing more than one carboxylic acid.

4. The insert of claim 3 wherein the compound containing more than one carboxylic acid is citric acid.

5. The ocular insert of claim 1, wherein the biologically active compound is ofloxacin or ibuprofen.

6. The ocular insert of claim 1, wherein the polyacid is selected from the group consisting of a polymer or copolymer of (meth)acrylic acid or (meth)acrylate.

7. The ocular insert of claim 4, wherein the polyacid is a copolymer of (meth)acrylic acid with (meth)acrylate.

8. The ocular insert of claim 1, wherein between 10 and 60 percent of carboxylic acid groups are bound to the biologically active compound.

9. The ocular insert of claim 1, wherein fatty acid residues are bound to the polyacid.

10. The ocular insert of claim 1, further comprising other polymers or additives.

11. The ocular insert of claim 10, wherein the polymers are selected from the group consisting of polyglycolic acid, collagen, polyorthoesters, polylactic acid, cellulose ester derivatives, dextran and its derivatives, albumin, gelatin, hyaluronic acid, amylose and its derivatives, poly(vinyl alcohol), maleic anhydride derivatives, and polyphosphazenes.

12. The ocular insert of claim 1 in the form of a film.

13. The ocular insert of claim 1 wherein the thickness of the device is between approximately 0.01 and 2 mm.

14. The ocular insert of claim 1, wherein the width of the insert is between approximately 5 and 100 $mm^2$.

15. The ocular insert of claim 1 wherein the carboxylic acid-containing compound is covalently bound to the poly-acid using a methylene diester bond.

16. The ocular insert of claim 1 further comprising a plasticizer.

17. The ocular insert of claim 16, wherein the plasticizer is selected from the group consisting of acetyl tri-n-butyl citrate, polyethylene glycol (600), epoxidized soybean oil, glycerol monoacetate, polyethylene glycol, propylene glycol dilaurate, decanol, dodecanol, 2-ethyl hexanol, 2,2-butoxyethanol ethylene glycol and tributyl citrate.

18. A method for the delivery of a biologically active substance comprising administering the substance in the ocular insert of claim 1.

* * * * *